(12) United States Patent
Nagino et al.

(10) Patent No.: US 9,519,822 B2
(45) Date of Patent: Dec. 13, 2016

(54) DETERMINATION METHOD, DETERMINATION DEVICE, DETERMINATION SYSTEM, AND COMPUTER PROGRAM

(71) Applicant: Toray Industries, Inc., Tokyo (JP)

(72) Inventors: Kunihisa Nagino, Kamakura (JP); Hiromichi Sasamoto, Otsu (JP); Shigeru Suzue, Otsu (JP)

(73) Assignee: Toray Industries, Inc. (JP)

( * ) Notice: Subject to any disclaimer, the term of this patent is extended or adjusted under 35 U.S.C. 154(b) by 142 days.

(21) Appl. No.: 14/383,601

(22) PCT Filed: Mar. 5, 2013

(86) PCT No.: PCT/JP2013/056020
§ 371 (c)(1),
(2) Date: Sep. 8, 2014

(87) PCT Pub. No.: WO2013/133283
PCT Pub. Date: Sep. 12, 2013

(65) Prior Publication Data
US 2015/0098611 A1    Apr. 9, 2015

(30) Foreign Application Priority Data

Mar. 8, 2012  (JP) ................... 2012-052311

(51) Int. Cl.
*G06K 9/00*       (2006.01)
*G01N 33/53*      (2006.01)
(Continued)

(52) U.S. Cl.
CPC ......... *G06K 9/0014* (2013.01); *G01N 33/5308* (2013.01); *G06K 9/4661* (2013.01);
(Continued)

(58) Field of Classification Search
CPC ............ G01N 33/5308; G01N 21/6458; G01N 33/543; G01N 21/6456; G06T 7/0012; G06T 2207/10056; G06T 2207/10064; G06T 2207/30072; G06K 9/0014; G06K 9/4661
(Continued)

(56) References Cited

U.S. PATENT DOCUMENTS 7,186,510 B2    3/2007  Yoshida
2001/0018183 A1*  8/2001  Bao ..................... C12Q 1/6837
                                                     435/6.13
(Continued)

FOREIGN PATENT DOCUMENTS

JP    2004-264289 A    9/2004
JP    2004-340574 A    12/2004
(Continued)

OTHER PUBLICATIONS

Genepix Pro 7 Software Users Guide downloaded on Mar. 17, 2016 from, http://mdc.custhelp.com/app/answers/detail/a_id/18792/~/genepix%C2%AE-pro-7-microarray-acquisition-%26-analysis-software-download-page.*
(Continued)

*Primary Examiner* — Bhavesh Mehta
*Assistant Examiner* — Narek Zohrabyan
(74) *Attorney, Agent, or Firm* — DLA Piper LLP (US)

(57) ABSTRACT

A determination method for determining reliability of a selective binding amount of a substance to be examined obtained as detection intensity of a label when a labeled substance to be examined binds to a selective binding substance fixed as a spot on a carrier includes: determining a position of the spot in image data obtained by imaging the detection intensity in the carrier and extracting a pixel group corresponding to the spot; calculating a ratio or a difference (Continued)

between a median value of the detection intensity of the pixel group extracted at the determining and a median value of the detection intensity of the pixel group excluding a certain top proportion of and/or a certain bottom proportion of pixels; and determining quality of the reliability based on the ratio or the difference calculated at the calculating and a certain reference value.

15 Claims, 12 Drawing Sheets

(51) Int. Cl.
    *G06T 7/00*     (2006.01)
    *G06K 9/46*     (2006.01)
    *G01N 21/64*     (2006.01)

(52) U.S. Cl.
    CPC ........ *G06T 7/0012* (2013.01); *G01N 21/6458* (2013.01); *G06T 2207/10056* (2013.01); *G06T 2207/10064* (2013.01); *G06T 2207/30072* (2013.01)

(58) Field of Classification Search
    USPC .................................. 382/128, 129, 103, 133
    See application file for complete search history.

(56) References Cited

U.S. PATENT DOCUMENTS

| | | | |
|---|---|---|---|
| 2003/0038812 A1* | 2/2003 | Bartell | B82Y 15/00 345/581 |
| 2003/0175720 A1 | 9/2003 | Bozinov et al. | |
| 2009/0041332 A1 | 2/2009 | Bhaskar et al. | |
| 2010/0130372 A1 | 5/2010 | Liu et al. | |
| 2010/0304997 A1 | 12/2010 | Yoshida et al. | |
| 2014/0307931 A1* | 10/2014 | Gierahn | G06T 7/0081 382/128 |

FOREIGN PATENT DOCUMENTS

| | | |
|---|---|---|
| JP | 2006-084281 A | 3/2006 |
| JP | 2008-039584 A | 2/2008 |
| JP | 2009-058356 A | 3/2009 |
| JP | 2009-236626 A | 10/2009 |
| JP | 2011-004737 A | 1/2011 |

OTHER PUBLICATIONS

Yang, Yee Hwa, Michael J. Buckley, and Terence P. Speed. "Analysis of cDNA microarray images." Briefings in bioinformatics 2.4 (2001): 341-349.*
Screenshots of GenePix Pro 7 software, four screenshots in total.*
Supplementary European Search Report dated Dec. 9, 2015 of corresponding European Application No. 13758079.1.
Reimers, M., et al., "Quality assessment of microarrays: Visualization of spatial artifacts and quantitation of regional biases," *BMC Bioinformatics*, vol. 6, No. 1, Jul. 1, 2005, pp. 166 (8 pages).
Zhao, Y., "Evaluation of normalization methods for two-channel microRNA microarrays," *Journal of Translational Medicine*, vol. 8, No. 1, Jul. 21, 2010, p. 69 (7 pages).
Inter Medical Co., Ltd., "GenePix Pro 7.0 Microarray Image Analysis," [online], Copyright 2006, Inter Medical Co., Ltd., [retrieved on Mar. 6, 2012], Internet URL:http://www.intermedical.cojp/homepage/products/axon/genepixpro7.html.

* cited by examiner

FIG. 13

| | Block | Column | Row | S_532_Median | M_TopCut Error_532 |
|---|---|---|---|---|---|
| 1 | 45 | 3 | 1 | 4941 | -22.5 |
| 2 | 45 | 3 | 8 | 5948 | -21.1 |
| 3 | 45 | 4 | 6 | 4676 | -20.8 |
| 4 | 45 | 21 | 22 | 6178 | -20.8 |
| 5 | 45 | 7 | 16 | 23774 | -19.4 |
| 6 | 45 | 23 | 19 | 2571 | -17.7 |
| 7 | 45 | 22 | 8 | 4269 | -17.1 |
| 8 | 45 | 2 | 8 | 16227 | -16.6 |
| 9 | 45 | 6 | 21 | 19029 | -16.6 |
| 10 | 45 | 14 | 9 | 2494 | -16.4 |
| 11 | 45 | 9 | 7 | 7260 | -16 |
| 12 | 45 | 3 | 19 | 2946 | -15.8 |
| 13 | 45 | 11 | 17 | 9011 | -15.3 |
| 14 | 45 | 19 | 20 | 3277 | -15.2 |
| 15 | 45 | 16 | 18 | 4134 | -15.1 |
| 16 | 45 | 4 | 18 | 2533 | -14.3 |
| 17 | 45 | 12 | 4 | 3278 | -14 |
| 18 | 45 | 9 | 4 | 2447 | -13.3 |
| 19 | 45 | 6 | 3 | 25154 | -13.1 |
| 20 | 45 | 19 | 21 | 7316 | -12.4 |
| 21 | 45 | 15 | 7 | 20093 | -12.2 |
| 22 | 45 | 6 | 14 | 2879 | -11.5 |
| 23 | 45 | 9 | 16 | 2124 | -11.4 |
| 24 | 45 | 20 | 7 | 5385 | -11.3 |
| 25 | 45 | 10 | 16 | 10653 | -10.5 |
| 26 | 45 | 13 | 14 | 2759 | -9.7 |
| 27 | 45 | 9 | 9 | 12019 | -9.3 |
| 28 | 45 | 1 | 15 | 15238 | -9.2 |
| 29 | 45 | 18 | 10 | 14139 | -8.6 |
| 30 | 45 | 1 | 20 | 36015 | -8.3 |
| 31 | 45 | 22 | 4 | 2414 | -8.2 |
| 32 | 45 | 19 | 11 | 3298 | -6.8 |
| 33 | 45 | 2 | 20 | 2393 | -5.8 |

FIG.14

| | Block | Column | Row | S_532_Median | M_Bottom CutError_532 |
|---|---|---|---|---|---|
| 1 | 45 | 23 | 19 | 2571 | 23.2 |
| 2 | 45 | 20 | 7 | 5385 | 22.8 |
| 3 | 45 | 4 | 6 | 4676 | 18.6 |
| 4 | 45 | 2 | 8 | 16227 | 17.8 |
| 5 | 45 | 3 | 8 | 5948 | 16.6 |
| 6 | 45 | 22 | 8 | 4269 | 15.1 |
| 7 | 45 | 12 | 4 | 3278 | 15 |
| 8 | 45 | 18 | 10 | 14139 | 14.9 |
| 9 | 45 | 3 | 1 | 4941 | 14.5 |
| 10 | 45 | 9 | 4 | 2447 | 14.1 |
| 11 | 45 | 19 | 20 | 3277 | 14 |
| 12 | 45 | 6 | 14 | 2879 | 13.9 |
| 13 | 45 | 9 | 7 | 7260 | 13.7 |
| 14 | 45 | 4 | 18 | 2533 | 13.3 |
| 15 | 45 | 6 | 3 | 25154 | 12.9 |
| 16 | 45 | 1 | 15 | 15238 | 12.9 |
| 17 | 45 | 19 | 11 | 3298 | 12.6 |
| 18 | 45 | 9 | 9 | 12019 | 12.4 |
| 19 | 45 | 16 | 18 | 4134 | 12.2 |
| 20 | 45 | 3 | 19 | 2946 | 11.8 |
| 21 | 45 | 22 | 4 | 2414 | 11.6 |
| 22 | 45 | 19 | 21 | 7316 | 11.3 |
| 23 | 45 | 21 | 22 | 6178 | 10.9 |
| 24 | 45 | 13 | 14 | 2759 | 10.8 |
| 25 | 45 | 15 | 7 | 20093 | 10.7 |
| 26 | 45 | 14 | 9 | 2494 | 10.1 |
| 27 | 45 | 6 | 21 | 19029 | 10 |
| 28 | 45 | 2 | 20 | 2393 | 9.7 |
| 29 | 45 | 11 | 17 | 9011 | 9.3 |
| 30 | 45 | 7 | 16 | 23774 | 8.2 |
| 31 | 45 | 10 | 16 | 10653 | 7.6 |
| 32 | 45 | 9 | 16 | 2124 | 7.5 |
| 33 | 45 | 1 | 20 | 36015 | 5.6 |

DETERMINATION METHOD, DETERMINATION DEVICE, DETERMINATION SYSTEM, AND COMPUTER PROGRAM

TECHNICAL FIELD

This disclosure relates to a determination method, a determination device, a determination system, and a computer program.

BACKGROUND

In recent years, a massive amount of genes, proteins, and the like have been enabled to be comprehensively analyzed according to development in technologies such as microarray or macroarray experiments. For example, in a DNA microarray, several hundreds to several tens of thousands of DNAs may be arrayed in a matrix to be fixed as spots on a carrier such as a slide glass, and mRNA or cDNA extracted and labeled from a cell to be examined may be hybridized with the spots to measure a gene expression level.

That is, a substance to be examined such as labeled cDNA selectively binds to a complementary DNA on the carrier so that the gene expression level can be estimated by acquiring a detection intensity of a label. Although reliability as data is required for a selective binding amount of the substance to be examined such as the gene expression level, the detection intensity may vary depending on non-biological factors such as when selective binding substances such as complementary DNAs fixed as spots on the carrier are unevenly distributed or a case in which dust is attached to a spot portion.

Accordingly, a method has been developed to determine uniformity of spots in a DNA microarray and the like. For example, a method of evaluating the uniformity disclosed in Japanese Patent Application Laid-open No. 2004-340574 includes the following steps: (1) background data corresponding to each of the spots is obtained by adapting analyzing software to an image obtained by scanning a monochromatic light emitting image of the DNA microarray, (2) plate-to-plate No. and a plate position of a target DNA corresponding to each of the spots are calculated, (3) the plate-to-plate No. and the plate position are allowed to correspond to each piece of the background data, and (4) the pieces of background data are arranged in the order of the plate No. and the plate position to obtain a sequence BG and a periodicity rule is detected by extracting a sub-sequence from the entire sequence.

Japanese Patent Application Laid-open No. 2008-039584 discloses that unevenness is evaluated with reference to a value of a coefficient of variation (CV). Therein, the CV of the spot means a proportion (%) of a standard deviation (SD) to an average value of fluorescence intensity of each spot that is obtained when the detection intensity of a spot of the DNA microarray and the like on the carrier is scanned and measured.

Regarding an analyzing software of microarray GenePix Pro (manufactured by Molecular Devices, LLC.), each intensity value of pixels included in the spot is compared to an average intensity value of pixels around the spot, and the spot is determined to be defective if a predetermined proportion of the pixels included in the spot satisfies the condition as follows: "(intensity of each pixel included in the spot)−(average intensity value of the pixels around the spot)<0" (Inter Medical Co., Ltd., "GenePix Pro 7.0 Microarray Image Analysis," [online], Copyright 2006 Inter Medical Co., Ltd., [retrieved on Mar. 6, 2012]. According to this, it is detected that a background around the spot becomes high due to certain abnormality, for example, dust is attached thereto or a chip is contaminated.

However, reliability of the selective binding amount of the substance to be examined cannot be appropriately determined by the method of determining the uniformity of spots in the art.

Specifically, although the uniformity among a plurality of spots can be evaluated by the method of evaluating the uniformity disclosed in JP '574, uniformity within single spot cannot be evaluated.

In the evaluating method with the CV value disclosed in JP '584, when intensity of some pixels in a pixel group configuring the spot is extremely high or low due to attachment of dust or the like, the standard deviation becomes large and the CV value exceeds a threshold. Accordingly, even though intensity data of the pixel group except for some pixels can be used, the data is eliminated, which causes excessive detection.

That is, in general, a median (median value) of the pixel group within the spot in an image is used as a representative value of signal intensity of a spot on a DNA chip and the like. For example, when alignment is performed in a circular spot having a diameter of 100 micrometers in the image, a median (spot median) of intensity is obtained for a pixel group of about 70 pixels (pixel size: 10 micrometers square) included in the circle.

This is because the median hardly varies depending on outliers as compared to using an average value of intensity of the pixel group. That is, when there are outliers such as an extremely large value and an extremely small value of the detection intensity of the pixel group in the spot, the overall average is skewed by the outliers.

FIG. 1 is a scatter plot illustrating detection intensity when the same substance to be examined is hybridized to two DNA chips. The horizontal axis represents the detection intensity of each spot in one of the DNA chips, and the vertical axis represents the detection intensity of each spot in the other DNA chip. That is, coordinates (X, Y) of one point represents detection intensity (X) measured in one DNA chip and detection intensity (Y) measured in the other DNA chip for the spot to which the same selective binding substance is fixed.

In that example, the same substance to be examined is hybridized to the two DNA chips so that ideally Y=X should be satisfied. However, as illustrated in FIG. 1, intensity plots of spots 1 and 2 are largely deviated from a line of Y=X so that it is considered that there is a defective spot. FIG. 2 is a diagram illustrating an intensity image of the spot 1 (left figure) and a variation graph of the detection intensity along the longitudinal line of the spot 1 (right figure). FIG. 3 is a diagram illustrating an intensity image of the spot 2 (left figure) and a variation graph of the detection intensity along the longitudinal line of the spot 2 (right figure). In the intensity image, a dashed-line circle indicates a spot portion, and the detection intensity is represented with a white gradation value.

As illustrated in the left figures of FIG. 2 and FIG. 3, the detection intensity is not represented as a uniform circle, but as a non-uniform gradation, in the intensity image of the spot portion. The variation graphs (right figures) represent a variation of the detection intensity along the longitudinal line of the spot portion in a range of one pixel in the horizontal direction and more than ten pixels in the longitudinal direction. Ideally, the detection intensity should be constant, but it largely varies. A main cause of the defect is a defective spot (a defect caused when the selective binding substance is fixed) and attachment of dust.

In the related art such as disclosed in JP '584, to eliminate such a defective spot, quality of the spot is determined using the CV value obtained as follows:

CV value=(standard deviation of intensity of pixel group)/(average value of intensity of pixel group).

That is, the data has been eliminated as a defective spot when the CV value is equal to or larger than a predetermined reference value. In that case, when 5 pixels in the pixel group including 70 pixels indicate extremely large values in the above example because dust and the like is attached to part of the spot, the CV value becomes equal to or larger than the reference value and the data is eliminated.

However, the median of the pixel group in the spot is usually used as the representative value of the signal intensity of the spot so that the value hardly varies even when the outlier is included in part of the spot. Accordingly, the data may be sufficiently usable. That is, in the conventional evaluating method using the CV value, sufficiently usable data has been eliminated by excessive detection of defective spot.

It could therefore be helpful to provide a determination method, a determination device, a determination system, and a computer program that can appropriately evaluate reliability of a selective binding amount of a substance to be examined considering non-biological effect for data obtained from a microarray experiment and the like.

SUMMARY

We thus provide:

A method of determining reliability of a selective binding amount of a substance to be examined obtained as detection intensity of a label when a labeled substance to be examined binds to a selective binding substance fixed as a spot on a carrier including: a pixel group extracting step of determining a position of the spot in image data obtained by imaging the detection intensity in the carrier and extracting a pixel group corresponding to the spot; a median calculating step of calculating a ratio or a difference between a median value of the detection intensity of the pixel group extracted at the pixel group extracting step and a median value of the detection intensity of the pixel group excluding a certain top proportion of and/or a certain bottom proportion of pixels; and a reliability determining step of determining quality of the reliability based on the ratio or the difference calculated at the median calculating step and a certain reference value.

Moreover, in the above-described method, a value of a ratio obtained from expression (1) and/or expression (2) is calculated at the median calculating step, the expressions (1) and (2) being as follows:

$$|X-Xt|/X \qquad (1)$$

$$|X-Xb|/X \qquad (2)$$

where X is a median value of the detection intensity of the pixel group, Xt is a median value of the detection intensity of the pixel group excluding the certain top proportion of pixels, and Xb is a median value of the detection intensity of the pixel group excluding the certain bottom proportion of pixels, and the reliability determining step determines that the reliability is defective when the value of the ratio calculated at the median calculating step is equal to or larger than the reference value.

Moreover, in the above-described method, the reference value is a value obtained from expression (3) as follows:

$$S=C+Z/X \qquad (3)$$

where S is the reference value, C is a constant, Z is an offset value corresponding to a sensitivity setting of a device for detecting the detection intensity of the label, and X is the median value of the detection intensity of the pixel group.

Moreover, in the above-described method, the device for detecting the detection intensity of the label is a photomultiplier, and the offset value is a value obtained from expression (4) as follows:

$$Z=X\hat{}(A)*B \qquad (4)$$

where Z is the offset value, X is a gain voltage of the photomultiplier, and A and B are constants.

Moreover, in the above-described method, the carrier is a microarray, the label is a fluorescent label, the detection intensity is a fluorescence amount, and the reliability determining step determines quality of the spot as the quality of the reliability.

A determination device includes at least a control unit determining reliability of a selective binding amount of a substance to be examined obtained as detection intensity of a label when a labeled substance to be examined binds to a selective binding substance fixed as a spot on a carrier, and the control unit includes: pixel group extracting means for determining a position of the spot in image data obtained by imaging the detection intensity in the carrier and extracting a pixel group corresponding to the spot; median calculating means for calculating a ratio or a difference between a median value of the detection intensity of the pixel group extracted by the pixel group extracting means and a median value of the detection intensity of the pixel group excluding a certain top proportion of and/or a certain bottom proportion of pixels; and reliability determining means for determining quality of the reliability based on the ratio or the difference calculated by the median calculating means and a certain reference value.

Moreover, the determination system is configured by connecting a detection device for reading detection intensity of a label, which is obtained when a labeled substance to be examined binds to a selective binding substance fixed as a spot on a carrier, to a determination device comprising at least a control unit for determining reliability of the selective binding amount of the substance to be examined obtained as the detection intensity, wherein the control unit of the determination device includes: image data acquisition means for acquiring, as imaged image data, the detection intensity in the carrier read via the detection device; pixel group extracting means for determining a position of the spot in the image data obtained by the image data acquisition means and extracting a pixel group corresponding to the spot; median calculating means for calculating a ratio or a difference between a median value of the detection intensity of the pixel group extracted by the pixel group extracting means and a median value of the detection intensity of the pixel group excluding a certain top proportion of and/or a certain bottom proportion of pixels; and reliability determining means for determining quality of the reliability based on the ratio or the difference calculated by the median calculating means and a certain reference value.

A computer program causes a computer comprising at least a control unit to execute a method of determining reliability of a selective binding amount of a substance to be examined obtained as detection intensity of a label when a labeled substance to be examined binds to a selective binding substance fixed as a spot on a carrier, wherein the control unit is caused to execute the method including: a pixel group extracting step of determining a position of the spot in image data obtained by imaging the detection intensity in the carrier and extracting a pixel group corresponding to the spot; a median calculating step of calculating a ratio or a difference between a median value of the detection intensity of the pixel group extracted at the pixel group extracting step and a median value of the detection intensity of the pixel group excluding a certain top proportion of and/or a certain bottom proportion of pixels; and a reliability determining step of determining quality of the reliability based on the ratio or the difference calculated at the median calculating step and a certain reference value.

We also provide a recording medium and the computer program described above is recorded therein.

With the determination method, the determination device, the determination system, and the computer program, reliability of the selective binding amount of the substance to be examined can be appropriately evaluated considering the non-biological effect in the data obtained from the microarray experiment and the like.

BRIEF DESCRIPTION OF THE DRAWINGS

FIG. 13 is a diagram illustrating a result obtained by sorting values of expression (1) obtained for each spot in ascending order.

FIG. 14 is a diagram illustrating a result obtained by sorting values of expression (2) obtained for each spot in descending order.

REFERENCE SIGNS LIST

Figure 1:
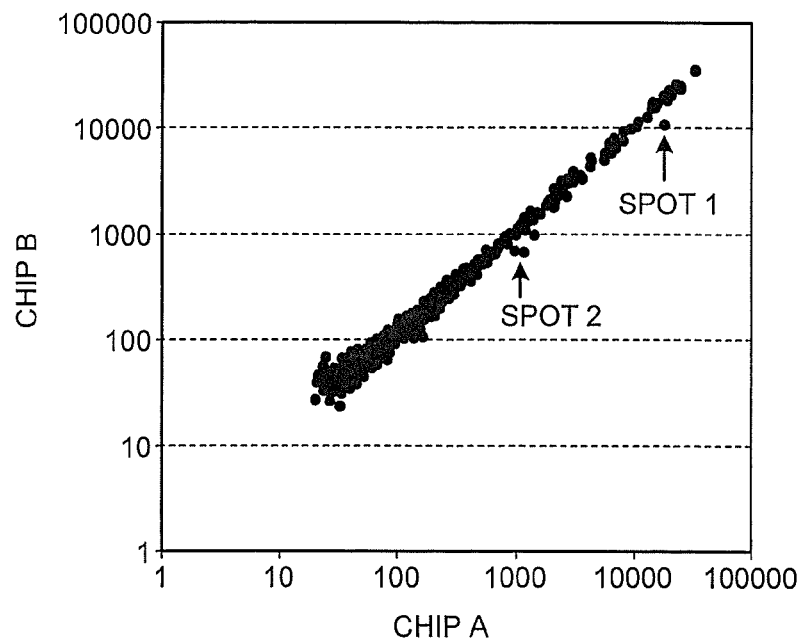
FIG. 1 is a scatter plot illustrating detection intensity when the same substance to be examined is hybridized to two DNA chips.

100 Determination device
102 Control unit
102a Image data acquisition unit
102b Pixel group extracting unit
102c Median calculation unit
102d Reliability determination unit
102e Reference value determination unit
104 Communication control interface unit
106 Storage unit
106a Image data file
106b Pixel group file
108 Input/output control interface unit
112 Input device
114 Output device
200 External system
300 Network

DETAILED DESCRIPTION

The following describes an example of a determination method, a determination device, a determination system, and a computer program in detail with reference to the drawings. Specifically, the example described below merely exemplifies our determination system and is not intended to limit this disclosure to be made with the determination system. The example may be equally applied to a determination method and a determination device according to other examples included in the scope of the appended claims. For example, although the following example may describe a determination method performed in the determination system, the example is not limited thereto. The determination method may be manually performed by a person. Although the following example describes a determination device connected to an input device of a measuring device and the like that acquires image data and the like, this disclosure is not limited thereto. The determination device may store the image data in a storage unit in advance without being connected to the input device and may acquire the image data from the outside via communication.

Overview

The following describes an overview of the example. Subsequently, a configuration, processing, and the like of the example will be described in detail with reference to the drawings.

We determine reliability of a selective binding amount of a substance to be examined obtained as detection intensity of a label when a labeled substance to be examined binds to a selective binding substance fixed as a spot on a carrier.

Herein, the "substance to be examined" means a sample directly or indirectly obtained from a cell, a tissue, and the like. Examples thereof include genomic DNA, RNA, cDNA, aRNA (RNA that is amplified using cDNA or a complementary sequence thereof as a template), protein, a sugar chain, and lipid. The "label" means a substance that can be detected by a detection unit. Examples thereof include a fluorescent label, a bioluminescent label, and a radioactive isotope label. The "selective binding substance" means a substance that selectively binds to a certain substance. Examples thereof include complementary DNA to DNA, complementary RNA to DNA, an antibody to an antigen, and an enzyme to a chemical substance.

The "carrier" may be a common substrate such as a DNA chip or a microarray. In addition, it may be a DNA chip substrate composed of polymethyl methacrylate having a rugged structure (3D-Gene (product name), manufactured and sold by Toray Industries, Inc. (corporate name), refer to Japanese Patent Application Laid-open No. 2004-264289). In this case, a projecting portion is spotted.

First, in this example, a position of the spot is determined in image data obtained by imaging detection intensity in the carrier and a pixel group corresponding to the spot is extracted. That is, a group of pixels constituting one spot portion on the image is extracted for each spot.

Subsequently, a ratio or a difference is calculated between a median value (X) of the detection intensity of the extracted pixel group and a median value (Xt/Xb) of the detection intensity of the pixel group excluding a predetermined top proportion and/or a predetermined bottom proportion of pixels. For example, the ratio may be calculated based on the expression (1) and/or expression (2) as follows:

$$|X-Xt|/X \qquad (1)$$

$$|X-Xb|/X \qquad (2)$$

where X is the median value of the detection intensity of the extracted pixel group, Xt is the median value of the detection intensity of the pixel group excluding a predetermined top proportion of pixels, and Xb is the median value of the detection intensity of the pixel group excluding a predetermined bottom proportion of pixels.

In examples described below, each of the predetermined top proportion and predetermined bottom proportion excluded in calculating Xt and Xb is 30% of the extracted pixel group. However, the proportion is not limited thereto. For example, the proportion may be an arbitrary value in a range of 20% to 40%.

Figure 2:
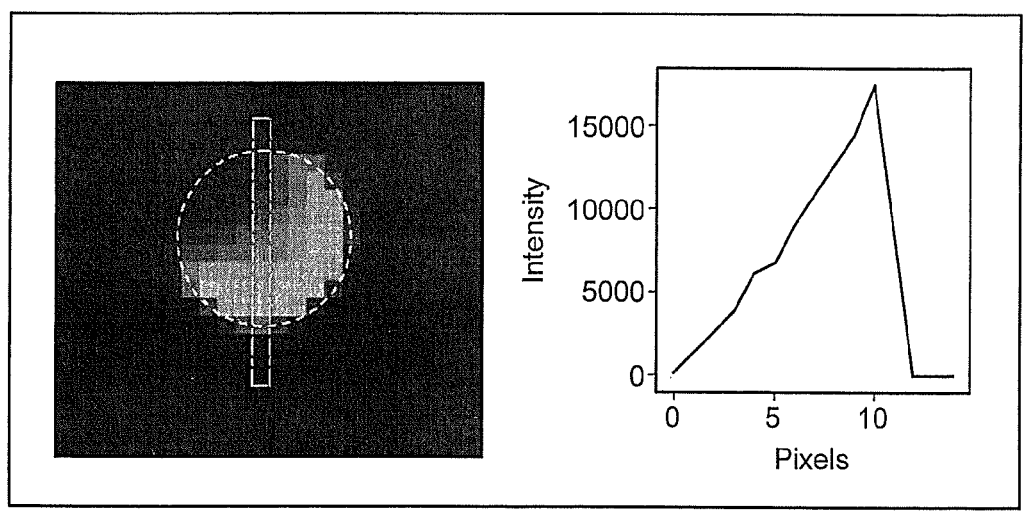
FIG. 2 is a diagram illustrating an intensity image of a spot 1 (left figure) and a variation graph of detection intensity along the longitudinal line of the spot 1 (right figure).
Figure 3:
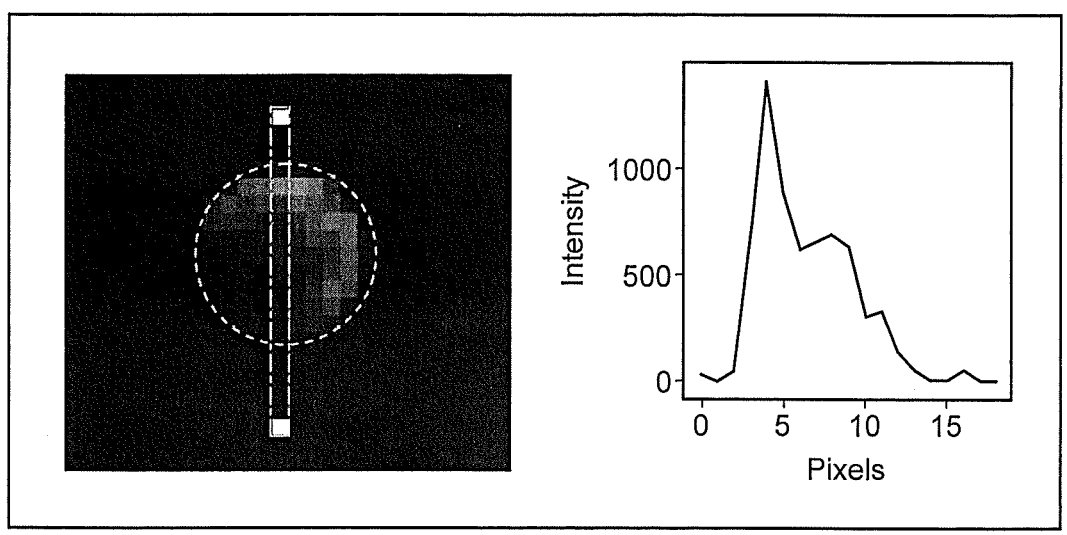
FIG. 3 is a diagram illustrating an intensity image of a spot 2 (left figure) and a variation graph of detection intensity along the longitudinal line of the spot 2 (right figure).

Quality of reliability is determined based on the calculated ratio or difference and a predetermined reference value S. For example, reliability may be determined to be defective when a value of the calculated ratio or difference is equal to or larger than the reference value S. In the spot 1 of FIG. 2, a value (%) of expression (1) was 34%, and a value (%) of expression (2) was 22.2%. In the spot 2 of FIG. 3, the value (%) of expression (1) was 30%, and the value (%) of expression (2) was 22.3%. Sufficient data can be obtained in both of the spots 1 and 2, the reference value S may be about 25% to 30% to not eliminate the data.

Herein, the reference value S may be a value obtained from expression (3) as follows:

$$S=C+Z/X \qquad (3)$$

where S is a reference value, C is a constant, Z is an offset value corresponding to a sensitivity setting of a device for detecting detection intensity of a label, and X is a median value of the detection intensity of the pixel group.

Herein, the offset value Z may be a value obtained from expression (4) as follows:

$$Z=X(A)*B \qquad (4)$$

where Z is an offset value, X is a gain voltage of a photomultiplier, and A and B are constants.

It is possible to appropriately evaluate the reliability of the selective binding amount of the substance to be examined considering the non-biological effect in the data obtained from the microarray experiment and the like. Specifically, it is possible to prevent sufficiently usable data from being eliminated by excessive detection, even though the data includes an outlier in part of the spot.

Configuration of Determination System

Figure 4:
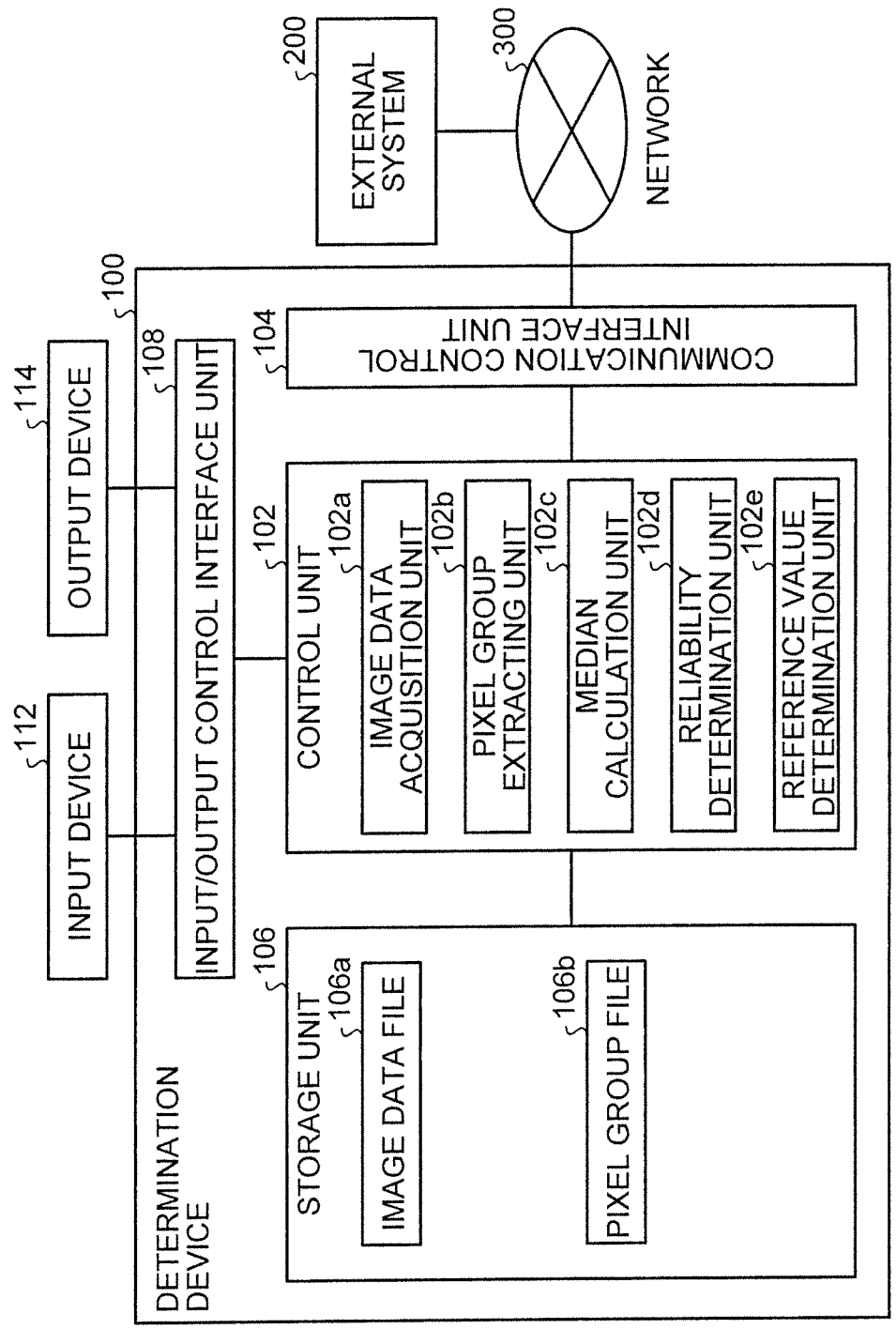
FIG. 4 is a block diagram illustrating an example of the entire structure of a determination system according to an example.

First, the following describes the configuration of the determination system. FIG. 4 is a block diagram illustrating an example of the entire structure of the determination system.

As illustrated in FIG. 4, the determination system generally includes an input device 112 that functions as a detection unit for reading detection intensity of a label, an output device 114, and a determination device 100.

The determination device 100 generally includes a control unit 102 such as a central processing unit (CPU) that integrally controls the entire determination device 100, a communication control interface unit 104 that is connected to a communication device (not illustrated) such as a router connected to a communication line and the like, an input/output control interface unit 108 that is connected to the input device 112 or the output device 114, and a storage unit 106 that stores therein various databases or tables. These units are communicably connected to each other via an arbitrary channel. Herein, as illustrated in FIG. 4, the determination device 100 may be connected to a network 300 via a communication device such as a router and a wired or wireless communication line such as a dedicated line. The determination device 100 may further be connected to an external system 200 via the network 300.

The various databases or tables stored in the storage unit 106 (an image data file 106a and a pixel group file 106b) may be storage means/device such as a fixed disk device. For example, the storage unit 106 may store therein various computer programs, tables, files, databases, Web pages, and the like that are used in various processes.

Among these components of the storage unit 106, the image data file 106a is an image data storage means/device that stores therein image data obtained by imaging the detection intensity in the carrier. For example, the image data stored in the image data file 106a may be image information obtained by scanning the detection intensity on a carrier plane by the detection unit. The image data file 106a may store therein the image data in advance, may be image data input from the input device 112 that functions as a detection unit described later, and may be image data received from the external system 200 via the network 300. By way of example, the image data file 106a stores therein, as the image data, gray-scale image data that uses the detection intensity as a gradation value.

The pixel group file 106b is a pixel group storage unit that stores therein information about the pixel group (such as intensity information) for each spot. For example, information to be stored in the pixel group file 106b is a value of the detection intensity (such as a gradation value) of each pixel, a median value of the pixel group, and the like associated with identification information that uniquely specifies the spot (a block number, a row number, a column number and the like of the carrier). For example, assuming that a carrier (biochip) is used, the carrier including four blocks in one biochip and being capable of detecting expression patterns of 64 (8×8) spots per block, that is, total of 256 genes, the pixel group file 106b stores therein a position at which a selective binding substance (such as a DNA fragment) corresponding to each of the genes (the block number, and the row number and the column number of the spot) is arranged in association with the gradation value and the like of the pixel group in the spot.

In FIG. 4, the input/output control interface unit 108 controls the input device 112 and the output device 114. As the output device 114, a printer, a recording medium output device, and the like may be used herein in addition to a monitor (including a home television). As the input device 112, a detection device (detection unit) that reads the detection intensity of the label may be used in addition to a keyboard, a mouse, and the like.

The "detection unit" means a unit that reads the detection intensity of the label obtained when the labeled substance to be examined binds to the selective binding substance fixed as the spot on the carrier. For example, the detection unit may be an examination unit for specifying the position at which the selective binding substance is spotted and acquiring the detection intensity, for example, a fluorescence microscope camera. When the label is a fluorescent label or a bioluminescent label, the detection unit may be a photomultiplier (photomultiplier tube). The detection unit is not limited to a unit that images the detection intensity such as the fluorescence microscope camera, and may be a unit that reads the detection intensity. The detection intensity may be imaged by the determination device 100 by scanning along the carrier plane. When the selective binding substance is DNA, a minute amount of double-stranded DNA binding fluorescent substance may be captured to detect the selective binding amount. The detection unit may also detect an absorption wavelength specific to the DNA. Also, when the selective binding substance is protein, a sugar chain, and the like, detection may be performed using the absorption wavelength, the fluorescent substance, a radioactive isotope (radioisotope), hybridization, a technique such as antigen-antibody reaction, and the like, corresponding to a property of the selective binding substance.

In FIG. 4, the control unit 102 includes a control program such as an operating system (OS), a computer program specifying various processing procedures, and an internal memory for storing required data, and performs information processing for executing various processes with these computer programs and the like. The control unit 102 conceptually includes an image data acquisition unit 102a, a pixel group extracting unit 102b, a median calculation unit 102c, a reliability determination unit 102d, and a reference value determination unit 102e.

Among these, the image data acquisition unit 102a is image data acquisition means that acquires image data obtained by imaging the detection intensity in the carrier. For example, the image data acquisition unit 102a may acquire, as the imaged image data, the detection intensity in the carrier that is read via the input device 112 functioning as the detection unit. The image data acquisition unit 102a may directly acquire the image data from the input device 112 such as the fluorescence microscope camera, and may image the detection intensity for each pair of coordinates obtained by causing the input device 112 such as the photomultiplier to scan along the carrier plane. The image data acquisition unit 102a may receive the image data from the external system 200 via the network 300. The image data acquisition unit 102a stores the acquired image data in the image data file 106a.

The pixel group extracting unit 102b is pixel group extracting means/device that determines the position of the spot in the image data stored in the image data file 106a and extracts the pixel group corresponding to the spot. For example, the pixel group extracting unit 102b may partition each spot portion on the image and extract a pixel group in each compartment based on an arrangement (such as spot center coordinates and a pixel radius) of the position (spot portion) on the carrier at which the selective binding substance is arranged. The pixel group extracting unit 102b may perform positioning by displaying the image data and arrangement pattern data on the output device 114 in a superposed manner and causing a user to perform input operation to move the displayed arrangement pattern via the input device 112 such as a mouse. The pixel group extracting unit 102b stores information about the pixel group (such as intensity information) for each spot in the pixel group file 106b. For example, the pixel group extracting unit 102b may store the value of the detection intensity (such as a gradation value) of each pixel in the pixel group file 106b in association with the identification information (the block number, the row number, the column number and the like of the carrier) that uniquely specifies the spot.

The median calculation unit 102c is median calculation means/device that calculates a ratio or a difference between the median value (X) of the detection intensity of the pixel group stored in the pixel group file 106b and the median value (Xt/Xb) of the detection intensity of the pixel group excluding a predetermined top proportion and/or a predetermined bottom proportion of pixels. For example, the ratio may be calculated based on expression (1) and/or expression (2). For example, the median calculation unit 102c may rearrange the detection intensity (such as a gradation value) of the pixel group in a certain spot stored in the pixel group file 106b by sorting in ascending order or descending order, and may obtain medium detection intensity of the group excluding a predetermined top proportion (x %) and medium detection intensity of the group excluding a predetermined bottom proportion (y %):

$$|X-Xt|/X \qquad (1)$$

$$|X-Xb|/X \qquad (2)$$

where X is the median value of the detection intensity of the extracted pixel group, Xt is the median value of the detection intensity of the pixel group excluding a predetermined top proportion of pixels, and Xb is the median value of the detection intensity of the pixel group excluding a predetermined bottom proportion of pixels.

The reliability determination unit 102d is reliability determination means that determines quality of reliability based on the ratio or the difference calculated by the median calculation unit 102c and the predetermined reference value. For example, when the ratio or the difference calculated by the median calculation unit 102c is equal to or larger than the reference value S, the reliability determination unit 102d may determine the reliability to be defective. The reliability determination unit 102d may exclude data of the defective spot from analysis based on the determination result of the reliability, and may output the determination result of the reliability to the output device 114. The control unit 102 may perform processing (such as exclusion of defective spot data) based on the determination result of the reliability by the reliability determination unit 102d and output a data analysis result to the output device 114. An output destination is not limited to a monitor as the output device 114. Alternatively, the result may be output to a printer or a recording medium and the like via a recording medium output device. The control unit 102 such as the reliability determination unit 102d may control the communication control interface unit 104 and transmit the determination result of the reliability and the analysis result data to the external system 200 via the network 300.

The reference value determination unit 102e is reference value determination means that determines a reference value as a reference of reliability determination by the reliability determination unit 102d. For example, the reference value determination unit 102e may determine the reference value S based on expression (3):

$$S = C + Z/X \quad (3)$$

where S is the reference value, C is the constant, Z is the offset value corresponding to the sensitivity setting of the device for detecting the detection intensity of the label, and X is the median value of the detection intensity of the pixel group.

Herein, the reference value determination unit 102e may determine the offset value Z in expression (3) based on expression (4):

$$Z = X^{(A)} * B \quad (4)$$

where Z is the offset value, X is the gain voltage of the photomultiplier, and A and B are constants.

In FIG. 4, the communication control interface unit 104 controls communication between the determination device 100 and the network 300 (or a communication device such as a router). That is, the communication control interface unit 104 has a function to communicate data to another terminal via a communication line. The network 300 has a function to connect the determination device 100 and the external system 200 to each other. Examples of the network 300 include the Internet. The external system 200 and the determination device 100 are connected to each other via the network 300. The external system 200 has a function to provide an external database or an external computer program related to detection intensity data of the label and the like.

The external system 200 may be configured as a server device such as a WEB server and an ASP server, or a terminal device. The hardware configuration thereof may include an information processing device such as a workstation and a personal computer being commercially available, and an auxiliary device thereof. Each function of the external system 200 is implemented with a CPU, a disk device, a memory device, an input device, an output device, a communication control device, and the like in the hardware configuration of the external system 200 and with a control program and the like that controls the above devices. The user of the determination device 100 may obtain data of detection intensity value, arrangement data, a computer program, and the like by accessing, via the network 300, an external database such as a detection intensity database related to a DNA chip and the like and a gene arrangement database provided by the external system 200, or a Web site that provides an external program such as a computer program for causing a determination method to be performed. The description about the configuration of the determination system and the determination device 100 is finished. Processing of determination device 100

Figure 5:
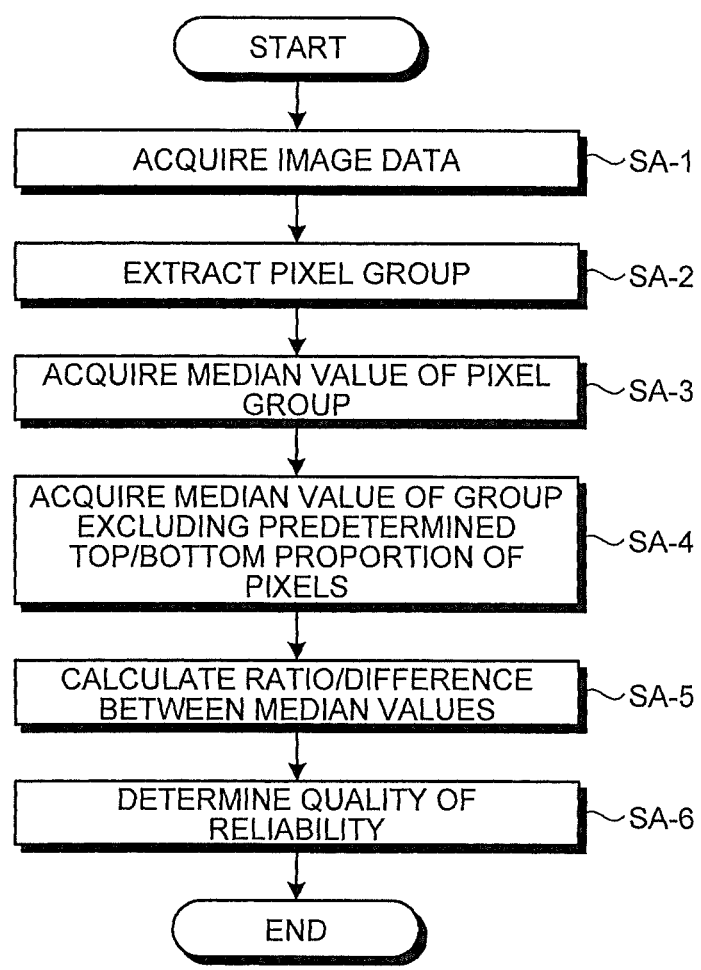
FIG. 5 is a flowchart illustrating an example of basic processing of a determination device 100 according to the example.

The following describes an example of the processing of the determination device 100 as described above in detail with reference to FIGS. 5 and 6. FIG. 5 is a flowchart illustrating an example of basic processing of the determination device 100.

First, as illustrated in FIG. 5, in the determination device 100, the image data acquisition unit 102a acquires image data obtained by imaging the detection intensity in the carrier and stores the acquired image data in the image data file 106a (Step SA-1). For example, the image data acquisition unit 102a may acquire, as imaged image data, the detection intensity in the carrier that is read via the input device 112 functioning as the detection unit. The image data acquisition unit 102a may directly acquire the image data from the input device 112 such as the fluorescence microscope camera, and may image the detection intensity for each pair of coordinates obtained by causing the input device 112 such as the photomultiplier to scan along the carrier plane. The image data acquisition unit 102a may read data from an external recording medium storing therein the detection intensity data or the image data via the input/output control interface unit 108.

The pixel group extracting unit 102b then determines the position of the spot in the image data stored in the image data file 106a, extracts the pixel group corresponding to the spot, and stores information about the extracted pixel group in the pixel group file 106b (Step SA-2). For example, the pixel group extracting unit 102b may partition each spot portion on the image and extract the pixel group in each compartment based on an arrangement (such as spot center coordinates and a pixel radius) of the position (spot portion) on the carrier at which the selective binding substance is arranged. The pixel group extracting unit 102b stores information about the pixel group (such as intensity information) for each spot in the pixel group file 106b. For example, the pixel group extracting unit 102b may store the value of the detection intensity (such as a gradation value) of each pixel in the pixel group file 106b in association with the identification information (the block number, the row number, the column number and the like of the carrier) that uniquely specifies the spot.

The median calculation unit 102c acquires the median value (X) of the detection intensity of the pixel group stored in the pixel group file 106b (Step SA-3). For example, the median calculation unit 102c may rearrange the detection intensity (such as a gradation value) of the pixel group in a certain spot by sorting in ascending order or descending order, and may obtain a medium (in the middle of a ranking) detection intensity value to obtain the median value (X).

Figure 6:
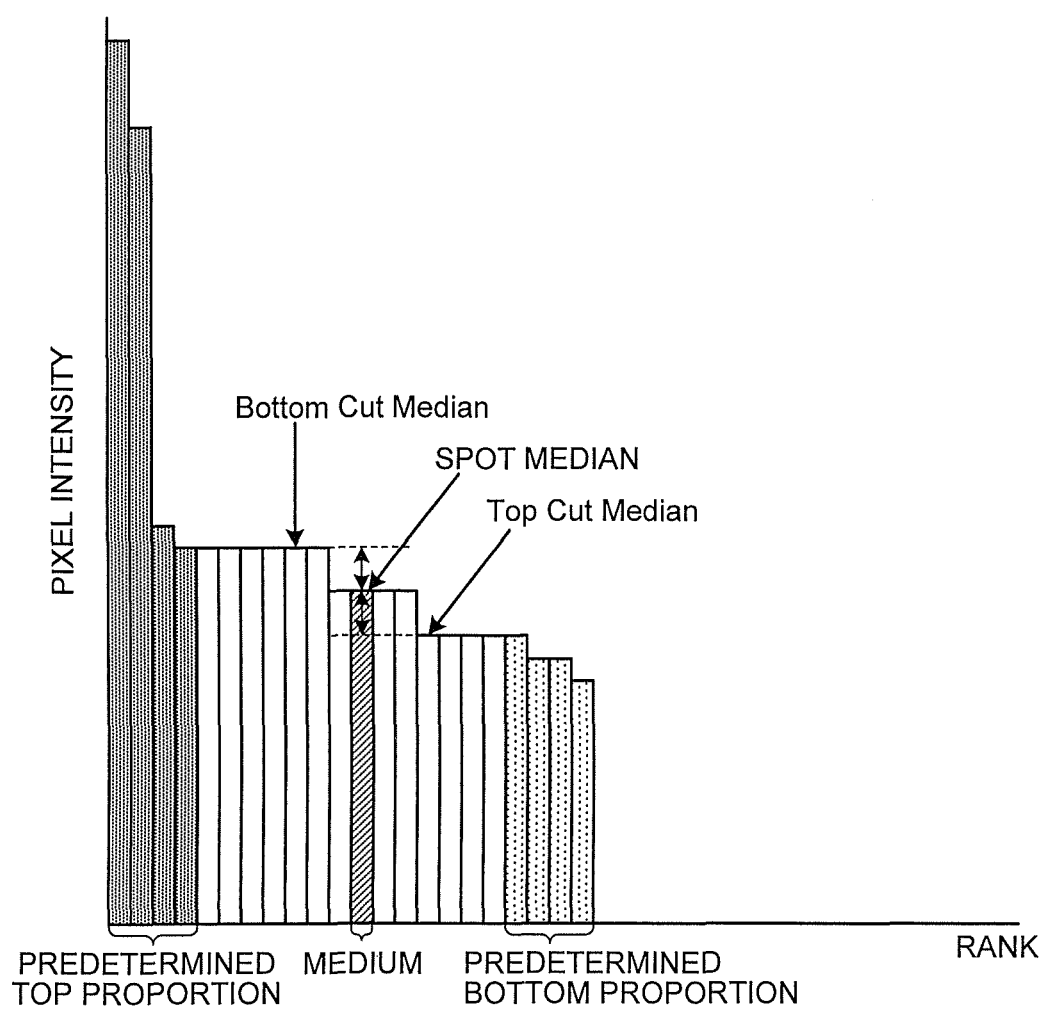
FIG. 6 is a diagram illustrating a relation among a spot median (X), a median excluding a predetermined top proportion (Xt: Top Cut Median), and a median excluding a predetermined bottom proportion (Xb: Bottom Cut Median).

The median calculation unit 102c acquires a median value (Xt) of the detection intensity of the pixel group stored in the pixel group file 106b excluding predetermined top proportion (x %) of pixels and/or a median value (Xb) of the detection intensity of the pixel group excluding a predetermined bottom proportion (y %) of pixels (Step SA-4). The predetermined top proportion (x %) and the predetermined bottom proportion (y %) may be, for example, 30%. By way of example, the median calculation unit 102c may rearrange the detection intensity (such as a gradation value) of the pixel group in a certain spot by sorting in ascending or descending order, and may obtain medium detection intensity (Xt) of the group excluding a predetermined top proportion (x %) and medium detection intensity (Xb) of the group excluding a predetermined bottom proportion (y %). FIG. 6 is a diagram illustrating a relation among a spot median (X), a median excluding a predetermined top proportion (Xt: Top Cut Median), and a median excluding a predetermined bottom proportion (Xb: Bottom Cut Median). Each bar in the bar graph corresponds to one pixel and the length thereof represents the detection intensity corresponding to the gradation value of the pixel. The pixel group in the spot is sorted in descending order according to the intensity along the horizontal axis.

As illustrated in FIG. 6, the spot median (X) is a medium (middle position) value in the ranking of intensity of the pixel group. The median Xt (Top Cut Median) is a value at the middle position in the pixel group excluding a predetermined top proportion (in this example, 4 pixels). The median Xb (Bottom Cut Median) is a value at the middle position in the pixel group excluding a predetermined bottom proportion (in this example, 4 pixels).

Returning to FIG. 5 again, the median calculation unit 102c calculates a ratio or a difference between the spot median X and the median Xt excluding the predetermined top proportion and/or a ratio or a difference between the spot median X and the median Xb excluding the predetermined bottom proportion (Step SA-5). Double-headed arrows in FIG. 6 represent a difference between the spot median X and the median Xt excluding the predetermined top proportion and a difference between the spot median X and the median Xb excluding the predetermined bottom proportion. The median calculation unit 102c may calculate the ratio based on expression (1) and/or expression (2):

$$|X-Xt|/X \qquad (1)$$

$$|X-Xb|/X \qquad (2)$$

where X is the median value of the detection intensity of the extracted pixel group, Xt is the median value of the detection intensity of the pixel group excluding a predetermined top proportion of pixels, and Xb is the median value of the detection intensity of the pixel group excluding a predetermined bottom proportion of pixels.

The reliability determination unit 102d determines quality of reliability based on the ratio or the difference calculated by the median calculation unit 102c and a predetermined reference value (Step SA-6). For example, when the ratio or the difference (such as an absolute value of the difference) calculated by the median calculation unit 102c is equal to or larger than the predetermined reference value S (%), the reliability determination unit 102d may determine the reliability to be defective. The reference value S (%) may be a constant value C (%). When white noise from an electric circuit system and the like cannot be ignored in a region having weak signal intensity, basic C (%) may be corrected by the reference value determination unit 102e (details will be described later).

An example of the basic processing of the determination device 100 has been described above.

Correction Processing of Reference Value

Figure 7:
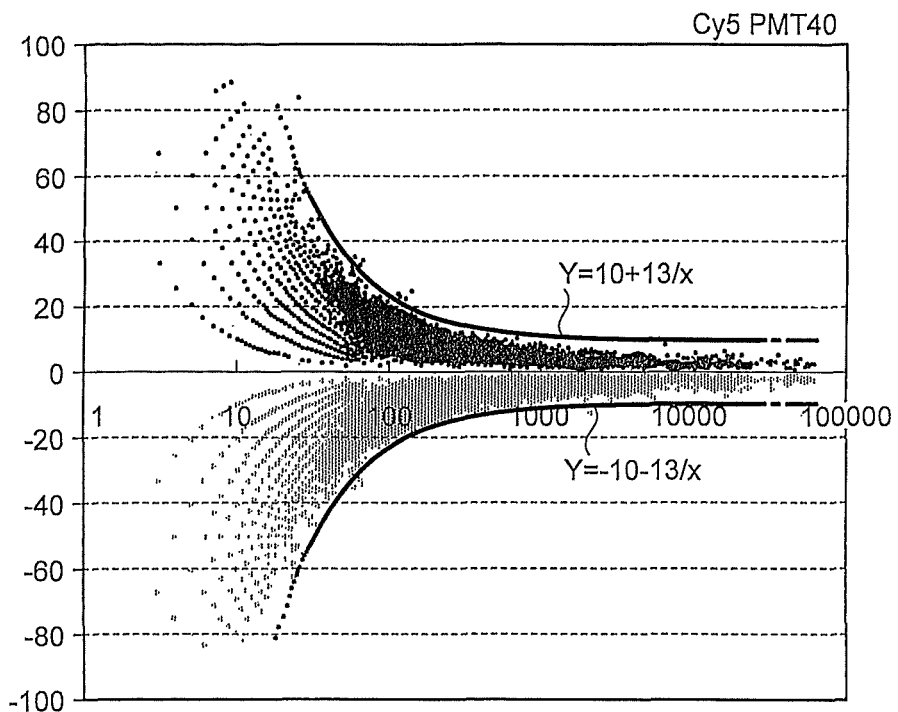
FIG. 7 is a diagram illustrating a correction curve and white noise in a region having weak signal intensity.

In the basic processing of the determination device 100 described above, the reference value S is assumed to be the constant value C. The following describes an example of correction processing in which the reference value determination unit 102e corrects and determines the reference value. FIG. 7 is a diagram illustrating a correction curve and white noise in a region having weak signal intensity. In FIG. 7, the horizontal axis indicates the spot median X representing the signal intensity, and the vertical axis indicates a value of the ratio obtained from expression (1) and expression (2). In this example, the absolute value is not obtained in expression (1) and expression (2). Accordingly, the value obtained from expression (2) is plotted in a positive region along the vertical axis, and the value obtained from expression (1) is plotted in a negative region therealong.

As illustrated in FIG. 7, the data becomes discrete as the signal intensity is reduced, influence of the white noise cannot be ignored, and the absolute value of the calculated ratio becomes large. Accordingly, it is preferable that the reference value S (%) is appropriately corrected rather than the constant value C (%). As a result of keen examination, we found a correction curve to correct the reference value S as follows: (Y=10+13/X, and Y=−10−13/X). A generalized expression thereof will be described below. That is, the reference value determination unit 102e may correct the basic C (%) to determine the reference value S based on expression (3):

$$S=C+Z/X \qquad (3)$$

where S is the reference value, C is the constant, Z is the offset value corresponding to the sensitivity setting of the device for detecting the detection intensity of the label, and X is the median value of the detection intensity of the pixel group.

Figure 8:
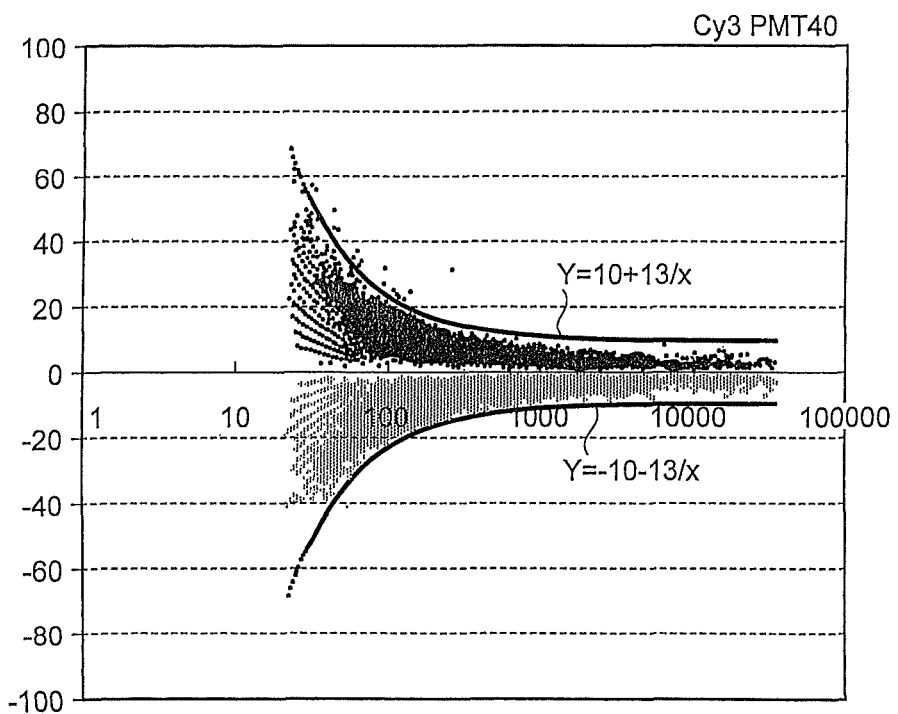
FIG. 8 is a diagram illustrating a result obtained by measuring the same carrier to which the same substance to be examined is provided when a photomultiplier tube (PMT) gain voltage (%) is set to "40" (40%×1 V).
Figure 9:
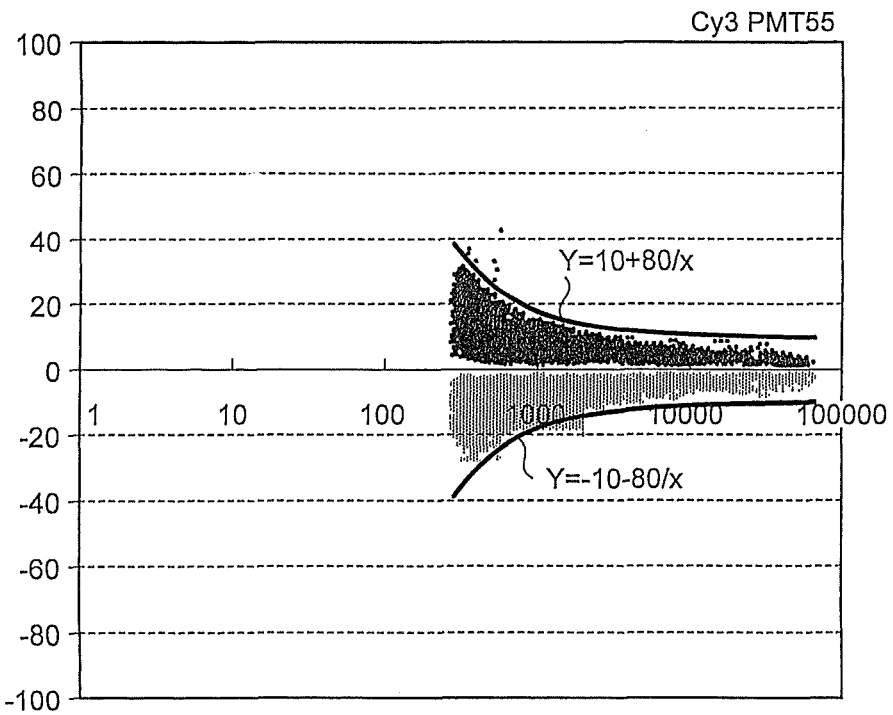
FIG. 9 is a diagram illustrating a result obtained by measuring the same carrier to which the same substance to be examined is provided when the PMT gain voltage (%) is set to "55" (55%×1 V).

Herein, the offset value Z is a constant value in the same setting. However, the offset value Z is changed when a gain setting of the photomultiplier in scanning is changed. FIGS. 8 and 9 are diagrams each illustrating a result obtained by measuring the same carrier to which the same substance to be examined is provided when the gain voltage (%) is set to "40" (in this case, a control voltage of the photomultiplier tube is as follows: 40%×1 V=0.4 V) and when it is set to "55" (55%×1 V=0.55 V).

As illustrated in FIGS. 8 and 9, a distribution state is changed when the gain voltage (sensitized control voltage) is changed. Accordingly, a threshold curve should be changed. The change depends on the offset value Z of a threshold curve as follows: S=C+Z/X. A preferable threshold curve can be obtained by setting the offset value to 13 in the example of FIG. 8, and by setting the offset value to 80 in the example of FIG. 9.

Figure 10:
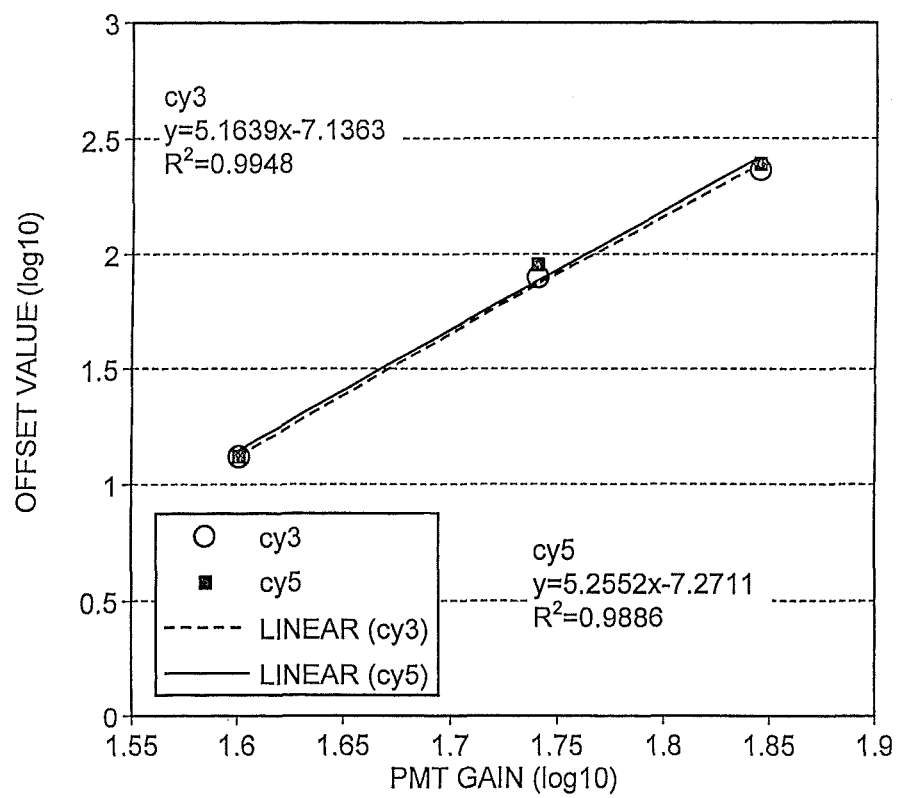
FIG. 10 is a graph plotting an offset value and the PMT gain voltage (sensitized control voltage).

FIG. 10 is a graph plotting the offset value and the gain voltage (sensitized control voltage). The horizontal axis indicates a logarithmic value of the gain voltage of the photomultiplier (PMT), and the vertical axis indicates the logarithmic value of the offset value.

As illustrated in FIG. 10, the offset value is changed depending on the gain voltage, and independent of a type of the label (cy3 and cy5). The logarithmic value of the offset value and the logarithmic value of the gain voltage are represented by a linear expression (the expression in FIG. 10). An inclination and an intercept are values specific to a scanner machine (photomultiplier). Expression (4) is obtained by generalizing a relational expression between the offset value and the gain voltage. That is, the reference value determination unit 102e may determine the offset value Z based on expression (4):

$$Z=X^{\wedge}(A)*B \qquad (4)$$

where Z is the offset value, X is the gain voltage of the photomultiplier, and A and B are constants. In the example of FIG. 10, the inclination of the graph is about 5.1639 to 5.12552, and the intercept thereof is about −7.1363 to −7.2711. That is, A ranges from about −7.1363 to −7.2711, and B ranges from about 5.1639 to 5.12552.

The description about the correction processing of the reference value is finished.

First Example

Figure 11:
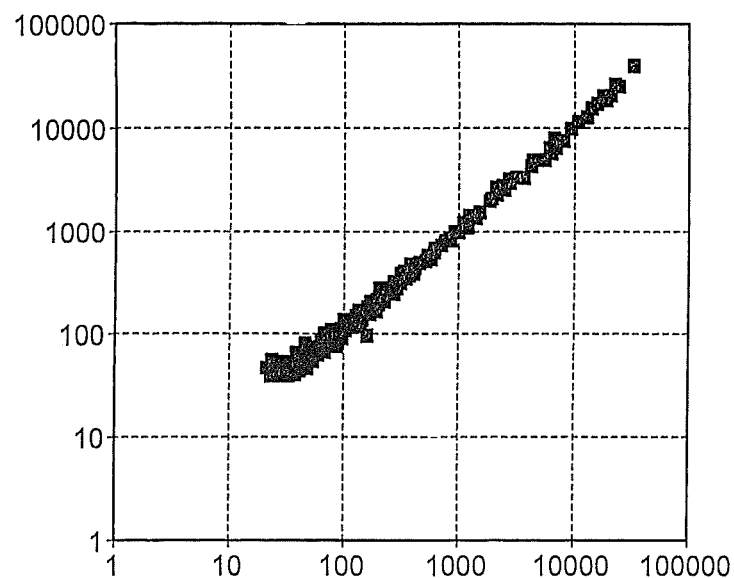
FIG. 11 is a scatter plot illustrating detection intensity when the same substance to be examined is hybridized to two DNA chips.

The following describes a first example in which an appropriate threshold was examined. First, the same substance to be examined was hybridized to two DNA chips to ensure that there is no significant difference in detection intensity thereof. FIG. 11 is a scatter plot illustrating the detection intensity when the same substance to be examined is hybridized to two DNA chips. The horizontal axis indicates the detection intensity of each spot in one DNA chip, and the vertical axis indicates the detection intensity of each spot in the other DNA chip.

Figure 12:
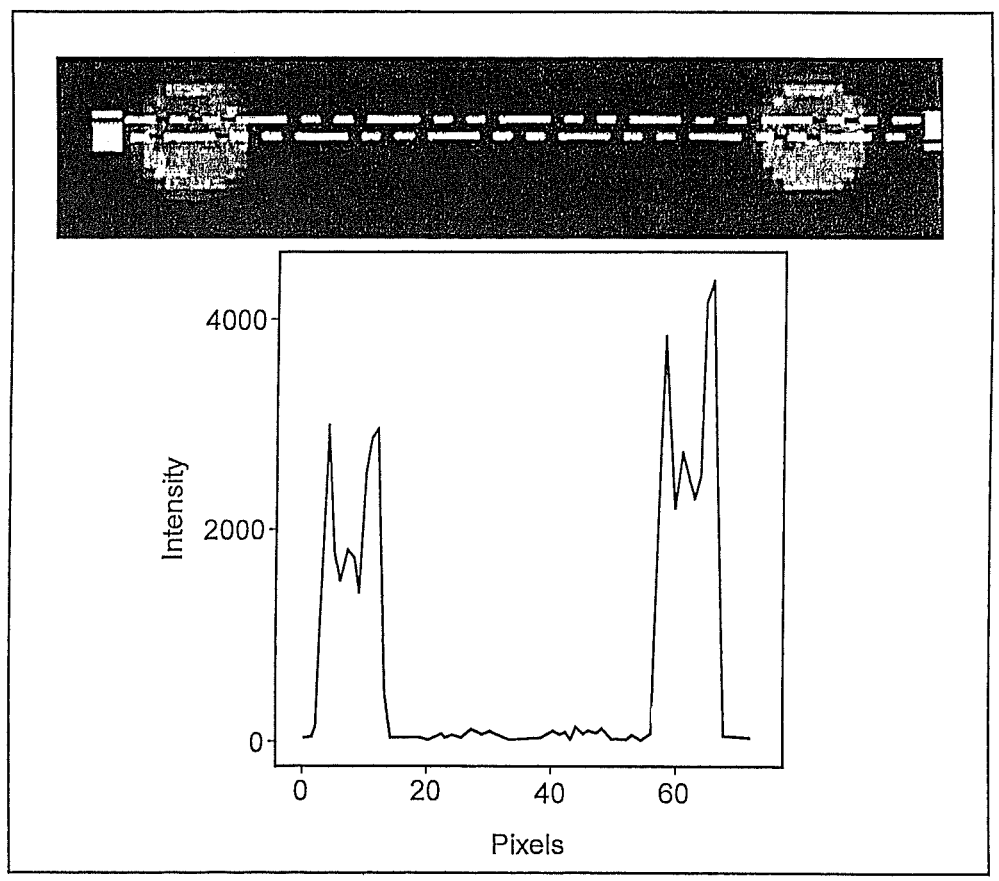
FIG. 12 is a diagram illustrating an intensity image of a spot of which inside is non-uniform (upper figure) and a variation graph of the detection intensity along a transverse line of the spot (lower figure).

As a result, as illustrated in FIG. 11, there was no significant difference in the detection intensity in the two DNA chips so that a normal state was ensured. As illustrated in FIG. 12, although there was a spot of which inside is non-uniform, the spot was not eliminated because it can be sufficiently usable as data when a median is used.

Subsequently, values of expression (1) and expression (2) was calculated for a spot of which detection intensity is a gain voltage set value "40" (control voltage of the photomultiplier tube is 40%×1 V) and the spot median thereof is equal to or larger than 2000 among these spots. The reason why the spot of which spot median is equal to or larger than 2000 was examined is that the white noise from an electric circuit and the like cannot be ignored in a portion having weak signal intensity as described above (for example, refer to FIGS. 7 and 8).

$$(X-Xt)/X*100(\%) \tag{1}$$

$$(X-Xb)/X*100(\%) \tag{2}$$

where X is the median value of the detection intensity of the pixel group, Xt is the median value of the detection intensity of the pixel group excluding a predetermined top proportion of pixels, and Xb is the median value of the detection intensity of the pixel group excluding a predetermined bottom proportion of pixels.

FIG. 13 is a diagram illustrating a result obtained by sorting values of expression (1) obtained for each spot in ascending order. FIG. 14 is a diagram illustrating a result obtained by sorting values of expression (2) obtained for each spot in descending order. Block represents the block number, Column represents the column number, and Row represents the row number. The spot is uniquely specified by these items. The item of S_532_Median represents the spot median.

As illustrated in FIGS. 13 and 14, it can be determined that unevenness due to a defective shape of the spot is not caused when the absolute value is equal to or smaller than 25% in both values of expression (1) and expression (2). Accordingly, it is considered that the absolute value of the reference value for determining quality of reliability is preferably about 25%.

Second Example

The following describes a second example in which an appropriate offset value was examined. In the second example, two chips of 3D-Gene (registered trademark) Human Ver1.1 (manufactured by Toray Industries, Inc.) were used as carriers. A series of procedures to hybridization was performed as described in a protocol using Human Reference RNA (manufactured by Stratagene corporation) as the substance to be examined. As the detection unit, 3D-Gene (registered trademark) Scanner (manufactured by Toray Industries, Inc.) was used.

Figure 15:
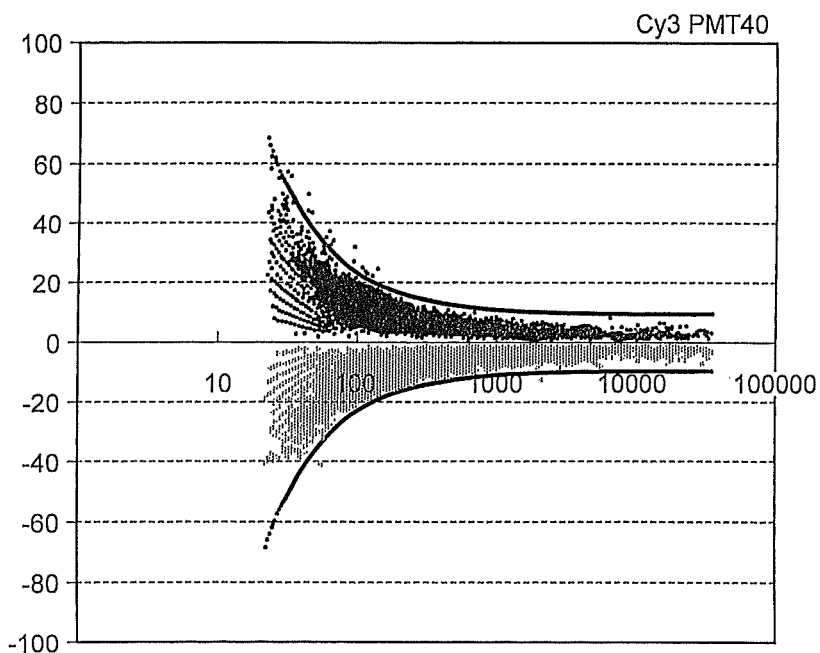
FIG. 15 is a scatter plot illustrating a result when the PMT gain voltage is set to 40%.
Figure 16:
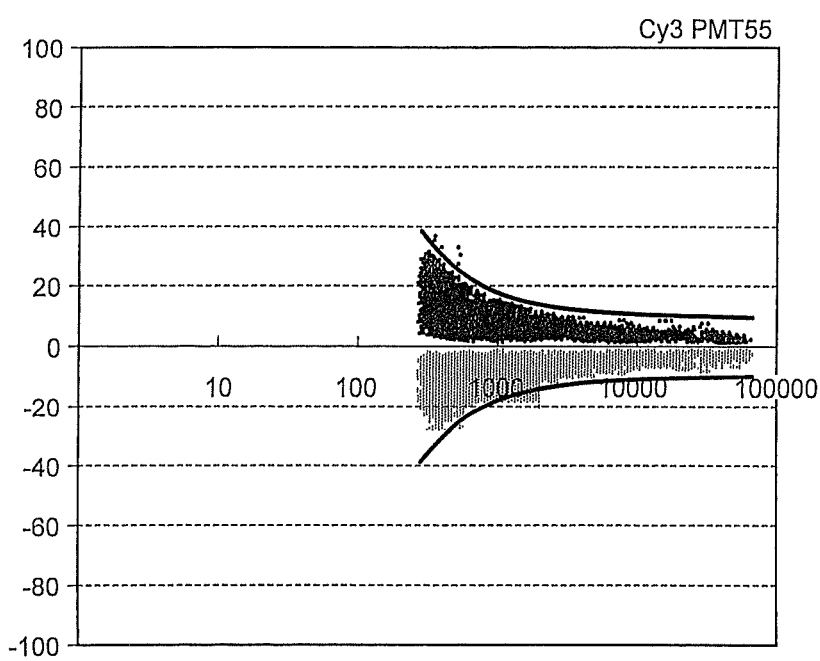
FIG. 16 is a scatter plot illustrating a result when the PMT gain voltage is set to 55%.
Figure 17:
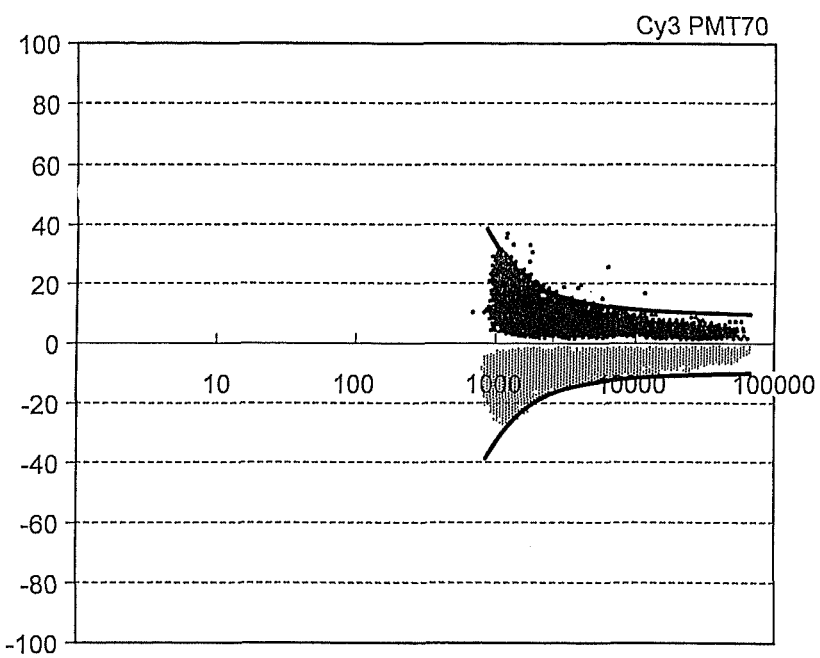
FIG. 17 is a scatter plot illustrating a result when the PMT gain voltage is set to 70%.

Measurement was performed for one of the two hybridized chips by changing a setting of a photomultiplier (PMT) of 3D-Gene (registered trademark) Scanner (manufactured by Toray Industries, Inc.) to 40%, 55%, and 70%, and the values of expression (1) and expression (2) were calculated for each spot. When the PMT setting is changed, a control voltage of the PMT is changed in proportion thereto. Accordingly, a photomultiplier tube gain is also changed. FIG. 15 is a scatter plot illustrating a result when the PMT setting is 40%, FIG. 16 is a scatter plot illustrating a result when the PMT setting is 55%, and FIG. 17 is a scatter plot illustrating a result when the PMT setting is 70%. A cut value is 30%, the spot median is plotted on the horizontal axis, and two values from expression (1) and expression (2) excluding calculation of the absolute value are plotted on the vertical axis.

For each of FIGS. 15 to 17, a curved line of $Y=\pm 10 \pm Z/X$ (X is the spot median, and Z is the constant) was depicted. The offset value Z in three conditions for the PMT was obtained so that the curved line reaches the bottom of spread of the two values from expression (1) and expression (2). As illustrated in FIGS. 15 to 17, the result shows that the offset value is 13 when the PMT setting is 40%, the offset value is 80 when the PMT setting is 55%, and the offset value is 230 when the PMT setting is 70%.

Figure 18:
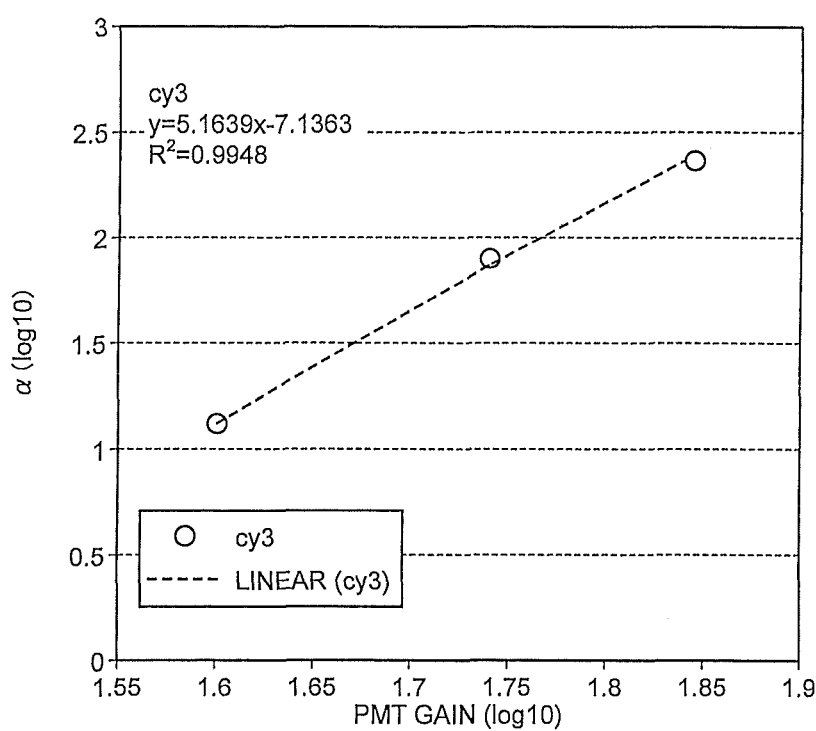
FIG. 18 is a logarithmic graph illustrating a correlation between a set value of the PMT gain voltage and an offset value.

Subsequently, a correlation between the PMT value and the offset value was examined. As illustrated in FIG. 18, it was demonstrated that a relation therebetween is represented by a straight line in a logarithmic graph. A correlation coefficient was equal to or larger than 0.99 so that validity of the correction was demonstrated. The following describes expression (4) for correcting the offset value:

$$Z=X^{\wedge}(A)*B \tag{4}$$

where Z is the offset value, and X is the gain voltage of the photomultiplier. In the second example, A was −7.13 and B was 5.16.

The description about the second example is finished.

As described above in detail, it is possible to provide the determination method, the determination device, the determination system, and the computer program that can appropriately evaluate the reliability of the selective binding amount of the substance to be examined considering non-biological effect for data obtained from the microarray experiment and the like. Accordingly, our methods, devices, systems and programs are especially available for fields such as medical care, medicine manufacture, development of new drugs, biological research, clinical testing, and for a biotechnology field and the like.

Other Examples

An example has been described above. Alternatively, our methods, devices, systems and programs may be implemented by various different examples within the scope of the subject matter described in the appended claims other than the examples described above.

Specifically, we describe an example of using DNA as the selective binding substance. However, the example is not limited thereto. A protein library such as an antibody, a compound library, and the like may be arranged as the selective binding substance. Material of the "carrier" is not limited to glass, and may be membranes or plastics.

In the above example, a fluorescent chemical substance (for example, Cy3 and Cy5) is used as the label. However, the example is not limited thereto. The label may be made by using a pigment without fluorescence property, a radioactive isotope, protein such as GFP and GRP, a His-tag, biotinylation, and the like.

In the above example, described is a case in which the determination device 100 performs processing on a standalone basis. Alternatively, the determination device 100 may be configured to perform processing in response to a request from a client terminal constituted with a housing separate from the determination device 100 and return the processing result thereof to the client terminal.

Among the pieces of processing, the entire or part of the processing described to be automatically performed can be manually performed. Alternatively, the entire or part of the processing described to be manually performed can be automatically performed using a known method. In addition, it is possible to arbitrarily change the processing procedure, the control procedure, the specific name, the information including registration data and the like of each piece of processing, and the database configuration described in the above-described literatures and figures unless otherwise specifically noted.

Each component of the determination device 100 is only schematically illustrated in the figures, and does not need to be physically configured as illustrated in the figures.

For example, the entire or arbitrary part of processing functions included in each device of the determination device 100, specifically, each processing function executed by the control unit 102 may be implemented by a CPU and a computer program that is interpreted and executed by the CPU, and may be implemented as hardware by wired logic. The computer program is recorded in a recording medium described later, and mechanically read by the determination device 100 as needed. That is, the storage unit 106 and the like such as a read only memory (ROM) or a hard disk (HD) records therein a computer program for giving a command to the CPU to perform various pieces of processing cooperating as an OS. This computer program is executed by being loaded on a random access memory (RAM), and configures the control device in cooperation with the CPU.

The computer program may be stored in an application program server connected to the determination device 100 via an arbitrary network 300, and the entire or part thereof can be downloaded as needed.

The computer program can be stored in a computer-readable recording medium. The "recording medium" includes any "portable physical medium" such as a memory card, a USB memory, an secure digital (SD) card, a flexible disk, a magneto-optical disc, a ROM, an erasable programmable read only Memory (EPROM), an electrically erasable programmable read only Memory (EEPROM), a compact disc (CD)-ROM, an magneto optical (MO), a digital versatile disc (DVD), and Blu-ray (registered trademark) Disc.

The "computer program" is a data processing method described using an arbitrary language or description method, and the format thereof such as a source code or a binary code does not matter. The "computer program" is not limited to a singular configuration. The "computer program" may have a distributed configuration as a plurality of modules or libraries, or implement the function thereof in cooperation with a separate computer program represented by the OS. In each device, a well-known configuration and procedure can be used as a specific configuration to read the recording medium, a reading procedure, an installation procedure after reading, or the like.

Various databases and the like (the image data file 106a to the pixel group file 106b) stored in the storage unit 106 are storage means including a memory device such as a RAM and a ROM, a fixed disk device such as a hard disk, a flexible disk, and a optical disc, and store therein various computer programs, tables, databases, and Web page files used for various pieces of processing and for providing a Web site.

The determination device 100 may also be configured as an information processing device such as a known personal computer, workstation, and the like, or may be configured by connecting any peripheral device to the information processing device. The determination device 100 may be made by installing software (including a computer program, data, and the like) that performs our method in the information processing device.

A specific form of distribution and integration of the devices is not limited to the form illustrated in the figures. The entire or part of the devices may be configured to be functionally or physically distributed/integrated in an arbitrary unit corresponding to various additions and the like, or corresponding to a functional load. That is, the examples described above may be arbitrarily combined to be performed, or the examples may be selectively performed.

The invention claimed is:

1. A method of determining reliability of a selective binding amount of a substance to be examined obtained as detection intensity of a label when a labeled substance to be examined binds to a selective binding substance fixed as a spot on a carrier, comprising:
    a pixel group extracting step of determining a position of the spot in image data obtained by imaging the detection intensity in the carrier and extracting a pixel group corresponding to the spot;
    a median calculating step of calculating a ratio of or a difference between 1) a median value of the detection intensity of the pixel group extracted at the pixel group extracting step and 2) a median value of the detection intensity of the pixel group excluding a certain top proportion of and/or a certain bottom proportion of pixels; and
    a reliability determining step of determining quality of the reliability based on the ratio or the difference calculated at the median calculating step and a certain reference value.

2. The method according to claim 1, wherein
    a value of a ratio obtained from expression (1) and/or expression (2) is calculated at the median calculating step, the expressions (1) and (2) being as follows:

$$|X-Xt|/X \quad (1)$$

$$|X-Xb|/X \quad (2)$$

where X is a median value of the detection intensity of the pixel group, Xt is a median value of the detection intensity of the pixel group excluding the certain top proportion of pixels, and Xb is a median value of the detection intensity of the pixel group excluding the certain bottom proportion of pixels,
    the reliability determining step determines that the reliability is defective when the value of the ratio obtained from at least one of expressions (1) and (2) is equal to or larger than the reference value.

3. The method according to claim 1, wherein
    the reference value is a value obtained from expression (3) as follows:

$$S=C+Z/X \quad (3)$$

where S is the reference value, C is a constant, Z is an offset value corresponding to a sensitivity setting of a device that detects the detection intensity of the label, and X is the median value of the detection intensity of the pixel group.

4. The method according to claim 3, wherein
    the device that detects the detection intensity of the label is a photomultiplier, and the offset value is a value obtained from expression (4) as follows:

$$Z = X(A) * B \quad (4)$$

where Z is the offset value, X is a gain voltage of the photomultiplier, and A and B are constants.

5. The method according to claim 1, wherein
the carrier is a microarray,
the label is a fluorescent label,
the detection intensity is a fluorescence amount, and
the reliability determining step determines quality of the spot as the quality of the reliability.

6. A determination device comprising at least a controller configured to determine reliability of a selective binding amount of a substance to be examined obtained as detection intensity of a label when a labeled substance to be examined binds to a selective binding substance fixed as a spot on a carrier, the control unit controller comprising a processor configured to:
determine a position of the spot in image data obtained by imaging the detection intensity in the carrier and extract a pixel group corresponding to the spot;
calculate a ratio of or a difference between 1) a median value of the detection intensity of the pixel group and 2) a median value of the detection intensity of the pixel group excluding a certain top proportion of and/or a certain bottom proportion of pixels; and
determine quality of the reliability based on the ratio or the difference and a certain reference value.

7. A determination system configured by connecting a detection device that reads detection intensity of a label, which is obtained when a labeled substance to be examined binds to a selective binding substance fixed as a spot on a carrier, to a controller configured to determine reliability of the selective binding amount of the substance to be examined obtained as the detection intensity, wherein
the controller comprises a processor configured to:
acquire, as imaged image data, the detection intensity in the carrier read via the detection device;
determine a position of the spot in the acquired image data and extract a pixel group corresponding to the spot;
calculate a ratio of or a difference between 1) a median value of the detection intensity of the pixel group and 2) a median value of the detection intensity of the pixel group excluding a certain top proportion of and/or a certain bottom proportion of pixels; and
determine quality of the reliability based on the ratio or the difference and a certain reference value.

8. A non-transitory computer readable recording medium on which an executable program is recorded, the program instructing a processor to execute determining reliability of a selective binding amount of a substance to be examined obtained as detection intensity of a label when a labeled substance to be examined binds to a selective binding substance fixed as a spot on a carrier, wherein the determining includes:
a pixel group extracting step of determining a position of the spot in image data obtained by imaging the detection intensity in the carrier and extracting a pixel group corresponding to the spot;
a median calculating step of calculating a ratio of or a difference between 1) a median value of the detection intensity of the pixel group extracted at the pixel group extracting step and 2) a median value of the detection intensity of the pixel group excluding a certain top proportion of and/or a certain bottom proportion of pixels; and
a reliability determining step of determining quality of the reliability based on the ratio or the difference calculated at the median calculating step and a certain reference value.

9. The determination method according to claim 2, wherein
the reference value is a value obtained from expression (3) as follows:

$$S = C + Z/X \quad (3)$$

where S is the reference value, C is a constant, Z is an offset value corresponding to a sensitivity setting of a device for detecting the detection intensity of the label, and X is the median value of the detection intensity of the pixel group.

10. The determination method according to claim 9, wherein
the device that detects the detection intensity of the label is a photomultiplier, and
the offset value is a value obtained from expression (4) as follows:

$$Z = X(A) * B \quad (4)$$

where Z is the offset value, X is a gain voltage of the photomultiplier, and A and B are constants.

11. The determination method according to claim 2, wherein
the carrier is a microarray,
the label is a fluorescent label,
the detection intensity is a fluorescence amount, and
the reliability determining step determines quality of the spot as the quality of the reliability.

12. The determination method according to claim 3, wherein
the carrier is a microarray,
the label is a fluorescent label,
the detection intensity is a fluorescence amount, and
the reliability determining step determines quality of the spot as the quality of the reliability.

13. The determination method according to claim 4, wherein
the carrier is a microarray,
the label is a fluorescent label,
the detection intensity is a fluorescence amount, and
the reliability determining step determines quality of the spot as the quality of the reliability.

14. The determination method according to claim 9, wherein
the carrier is a microarray,
the label is a fluorescent label,
the detection intensity is a fluorescence amount, and
the reliability determining step determines quality of the spot as the quality of the reliability.

15. The determination method according to claim 10, wherein
the carrier is a microarray,
the label is a fluorescent label,
the detection intensity is a fluorescence amount, and
the reliability determining step determines quality of the spot as the quality of the reliability.

* * * * *